US012565654B2

(12) United States Patent
Ochiya et al.

(10) Patent No.: US 12,565,654 B2
(45) Date of Patent: Mar. 3, 2026

(54) EXTRACELLULAR VESICLE SECRETION REDUCING AGENT FOR REDUCING EXTRACELLULAR VESICLE SECRETION, AND USE OF THE SAME

(71) Applicant: THEORIA SCIENCE INC., Tokyo (JP)

(72) Inventors: Takahiro Ochiya, Tokyo (JP); Fumihiko Urabe, Tokyo (JP); Nobuyoshi Kosaka, Tokyo (JP); Tomofumi Yamamoto, Tokyo (JP)

(73) Assignee: THEORIA SCIENCE INC., Tokyo (JP)

( * ) Notice: Subject to any disclaimer, the term of this patent is extended or adjusted under 35 U.S.C. 154(b) by 744 days.

(21) Appl. No.: 17/995,550

(22) PCT Filed: Apr. 7, 2021

(86) PCT No.: PCT/JP2021/014693
§ 371 (c)(1),
(2) Date: Oct. 5, 2022

(87) PCT Pub. No.: WO2021/206105
PCT Pub. Date: Oct. 14, 2021

(65) Prior Publication Data

US 2023/0151368 A1 May 18, 2023

(30) Foreign Application Priority Data

Apr. 7, 2020 (JP) ................................ 2020-069392
Feb. 16, 2021 (JP) ................................ 2021-022825

(51) Int. Cl.

| | |
|---|---|
| ***C12N 15/113*** | (2010.01) |
| ***A61P 1/00*** | (2006.01) |
| ***A61P 1/18*** | (2006.01) |
| ***A61P 7/00*** | (2006.01) |
| ***A61P 11/00*** | (2006.01) |
| ***A61P 17/00*** | (2006.01) |
| ***A61P 35/00*** | (2006.01) |
| ***A61P 35/04*** | (2006.01) |

(52) U.S. Cl.
CPC ............ *C12N 15/1137* (2013.01); *A61P 1/00* (2018.01); *A61P 1/18* (2018.01); *A61P 7/00* (2018.01); *A61P 11/00* (2018.01); *A61P 17/00* (2018.01); *A61P 35/00* (2018.01); *A61P 35/04* (2018.01); *C12N 2310/14* (2013.01); *C12N 2310/141* (2013.01)

(58) Field of Classification Search
CPC .............. C12N 15/1137; C12N 15/111; C12N 2310/14; C12N 2310/141; C12N 2320/12; A61P 35/00; A61P 35/04; A61P 11/00; A61P 17/00
USPC ....... 514/44 A, 44 R; 424/9.1; 435/6.1, 91.1, 435/91.31, 455, 458; 530/300, 350; 536/23.1, 24.5
See application file for complete search history.

(56) References Cited

U.S. PATENT DOCUMENTS

| | | | |
|---|---|---|---|
| 2014/0045915 A1 | 2/2014 | Skog et al. |
| 2018/0177699 A1 | 6/2018 | Bin et al. |
| 2019/0071400 A1 | 3/2019 | Mainolfi |
| 2019/0185851 A1 | 6/2019 | Ochiya et al. |

FOREIGN PATENT DOCUMENTS

| | | |
|---|---|---|
| CN | 106562951 B | 2/2020 |
| EP | 3348278 A1 | 7/2018 |
| JP | 2018-521038 | 8/2018 |
| WO | 2010051532 A1 | 5/2010 |
| WO | 2012/031008 | 3/2012 |
| WO | 2017/003114 | 1/2017 |
| WO | 2017/043370 | 3/2017 |
| WO | 2019/106126 | 6/2019 |
| WO | 2020/043716 | 3/2020 |

OTHER PUBLICATIONS

Rathore et al., “Metabolic compensation activates pro-survival mTORC1 signaling upon 3-phosphoglycerate dehydrogenase inhibition in osteosarcoma”, Cell Reports, Jan. 26, 2021, vol. 34, Issue 4, 108678, 22 pages.
Yamamoto et al., “Aberrant regulation of serine metabolite drives extracellular vesicle release and cancer progression”. bioRxiv, 2022, 491299, 41 pages.
Elsaadi et al., “Targeting phosphoglycerate dehydrogenase in multiple myeloma”, Exp HematolOncol., 2021, 10:3, 13 pages.
International Search Report issued in International Application No. PCT/JP2021/014693, Jun. 15, 2021, 8 pages w/translation.
Office Action issued in the corresponding Chinese patent application No. 202180026707.8, Aug. 5, 2024, 19 pages w/translation.
Pacold, et al., “A PHGDH inhibitor reveals coordination of serine synthesis and one carbon unit fate”, Nature Chemical Biology, Jun. 2016 (published online Apr. 25, 2016), vol. 12, pp. 452-458.
Dong, et al., “MicroRNA-891b is an independent prognostic factor of pancreatic cancer by targeting Cbl-b to suppress the growth of pancreatic cancer cells”, Oncotarget, Aug. 2016, vol. 7, No. 50, pp. 82338-82353.
Metcalf, “Investigation of phosphoserine aminotransferase 1(PSAT1) in breast cancer progression”, Electronic Theses and Dissertations of the University of Louisville, Dec. 2019, pp. 1-129, (https://doi.org/10.18297/etd/3345).
Zhou Ye, et al., “Serine Biosynthesis Pathway Mediated the Adaptive Resistance to EGFR-TKIs in Lung Adenocarcinoma”, Progress in Modern Biomedicine, Sep. 2019, vol. 19, No. 17, pp. 3218-3224—Abstract.

(Continued)

*Primary Examiner* — Jane J Zara
(74) *Attorney, Agent, or Firm* — HSML P.C.

(57) ABSTRACT

The present invention provides a novel secretion reducing agent and novel secretion reducing method for reducing extracellular vesicle secretion from cells. The extracellular vesicle secretion reducing agent of the present invention is characterized in that it contains an inhibitor of a serine synthesis pathway. The cells are, for example, cancer cells such as colorectal cancer cells, lung cancer cells, melanoma cells, breast cancer cells, pancreas cancer cells, and multiple myeloma cells.

4 Claims, 12 Drawing Sheets

Specification includes a Sequence Listing.

(56) References Cited

OTHER PUBLICATIONS

Chen, et al., "Beijing: Peking Union Medical College Press", Pharmacology of New Drugs, Dec. 31, 2010, p. 60—See the translation of the Chinese Office Action for a concise explanation.
Possemato, et al., "Functional genomics reveal that the serine synthesis pathway is essential in breast cancer", Nature, vol. 476, Aug. 18, 2011, pp. 346-350 (8 total pages).
Bobrie, et al., "Exosome Secretion: Molecular Mechanisms and Roles in Immune Responses", Traffic 2011, vol. 12, pp. 1659-1668.
Office Action issued in corresponding Korean Patent Application 10-2022-7032794, Dec. 17, 2024, 15 pages w/translation.
The extended European search report issued in European Application No. 21784748.2, mailed Apr. 17, 2025.
Jinlong Liu et al., "Phosphoglycerate dehydrogenase induces glioma cells proliferation and invasion by stabilizing forkhead box M1—PubMed", Dec. 11, 2012 (Dec. 11, 2012), XP093260428, DOI: 10.1007/s11060-012-1018-x.Epub Retrieved from the Internet: URL:https://pubmed.ncbi.nlm.nih.gov/23229761/.
Sirkku Pollari et al., "Enhanced serine production by bone metastatic breast cancer cells stimulates osteoclastogenesis", Breast Cancer Res Treat, 2011, vol. 125, No. 2, pp. 421-430, XP019868281 (Epub Mar. 30, 2010).
Yung-Chieh Chan et al., "Overexpression of PSAT1 promotes metastasis of lung adenocarcinoma by suppressing the IRFI-IFNy axis", Oncogene, 2020, vol. 39, No. 12, pp. 2509-2522, XP037070491 (Epub Jan. 27, 2020).
Tomofumi Yamamoto et al., "Aberrant regulation of serine metabolism drives extracellular vesicle release and cancer progression", Cell Reports, 2024, vol. 43, No. 8, 43 pages provided, XP093263688 (Aug. 27, 2024).

EXTRACELLULAR VESICLE SECRETION REDUCING AGENT FOR REDUCING EXTRACELLULAR VESICLE SECRETION, AND USE OF THE SAME

TECHNICAL FIELD

The present invention relates to an extracellular vesicle secretion reducing agent for reducing extracellular vesicle secretion from cells and the use of the same.

BACKGROUND ART

In recent years, extracellular vesicles such as exosomes secreted from cells have been attracting attention. Extracellular vesicles contain nucleic acids, such as microRNA (miRNA), and proteins. The extracellular vesicles mediate the transfer of their inclusions to a recipient cell from a cell that has secreted these extracellular vesicles and thus are considered to function as a cell-to-cell communication tool. Specifically, for example, it has been reported that extracellular vesicles secreted from the primary cancer are involved in cancer metastasis.

SUMMARY OF INVENTION

Technical Problem

However, the mechanism of their secretion, namely, how the extracellular vesicle secretion from cells is regulated, has not yet been clarified. If the mechanism of extracellular vesicle secretion is clarified, it becomes possible to easily analyze the influence of secretion of extracellular vesicles on a living organism by, for example, reducing the secretion of the extracellular vesicles on the basis of this mechanism. Further, reducing the secretion of extracellular vesicles on the basis of the mechanism also enables the treatment of diseases and the like caused by the secretion of the extracellular vesicles.

In light of the foregoing, it is an object of the present invention to provide a novel secretion reducing agent and novel secretion reducing method for reducing extracellular vesicle secretion from cells.

Solution to Problem

In order to achieve the above object, the present invention provides an extracellular vesicle secretion reducing agent for reducing extracellular vesicle secretion from a cell, containing: an inhibitor of a serine synthesis pathway.

The present invention also provides a method for reducing extracellular vesicle secretion from a cell, including: administering, to an administration target, the extracellular vesicle secretion reducing agent of the present invention.

The present invention also provides a screening method for a candidate substance for an extracellular vesicle secretion reducing agent for reducing extracellular vesicle secretion from a cell, including: selecting, out of test substances, an inhibitory substance that inhibits a serine synthesis pathway as a candidate substance that reduces extracellular vesicle secretion from a cell.

Advantageous Effects of Invention

The inventors of the present invention found through in-depth studies that the serine synthesis pathway is involved in extracellular vesicle secretion from cells, and thus inhibiting the serine synthesis pathway can reduce the extracellular vesicle secretion from cells. The mechanism of extracellular vesicle secretion from cells has not yet been clarified as described above, and the above finding was first discovered by the inventors of the present invention. According to the present invention, extracellular vesicle secretion from cells can be reduced by inhibiting the serine synthesis pathway. Thus, reducing the secretion according to the present invention also enables, for example, analysis of the influence of the extracellular vesicle secretion or the influence of reducing the extracellular vesicle secretion on a living organism. Therefore, it can be said that the present invention provides very useful technology in the medical field, for example.

DESCRIPTION OF EMBODIMENTS

Figure 1:
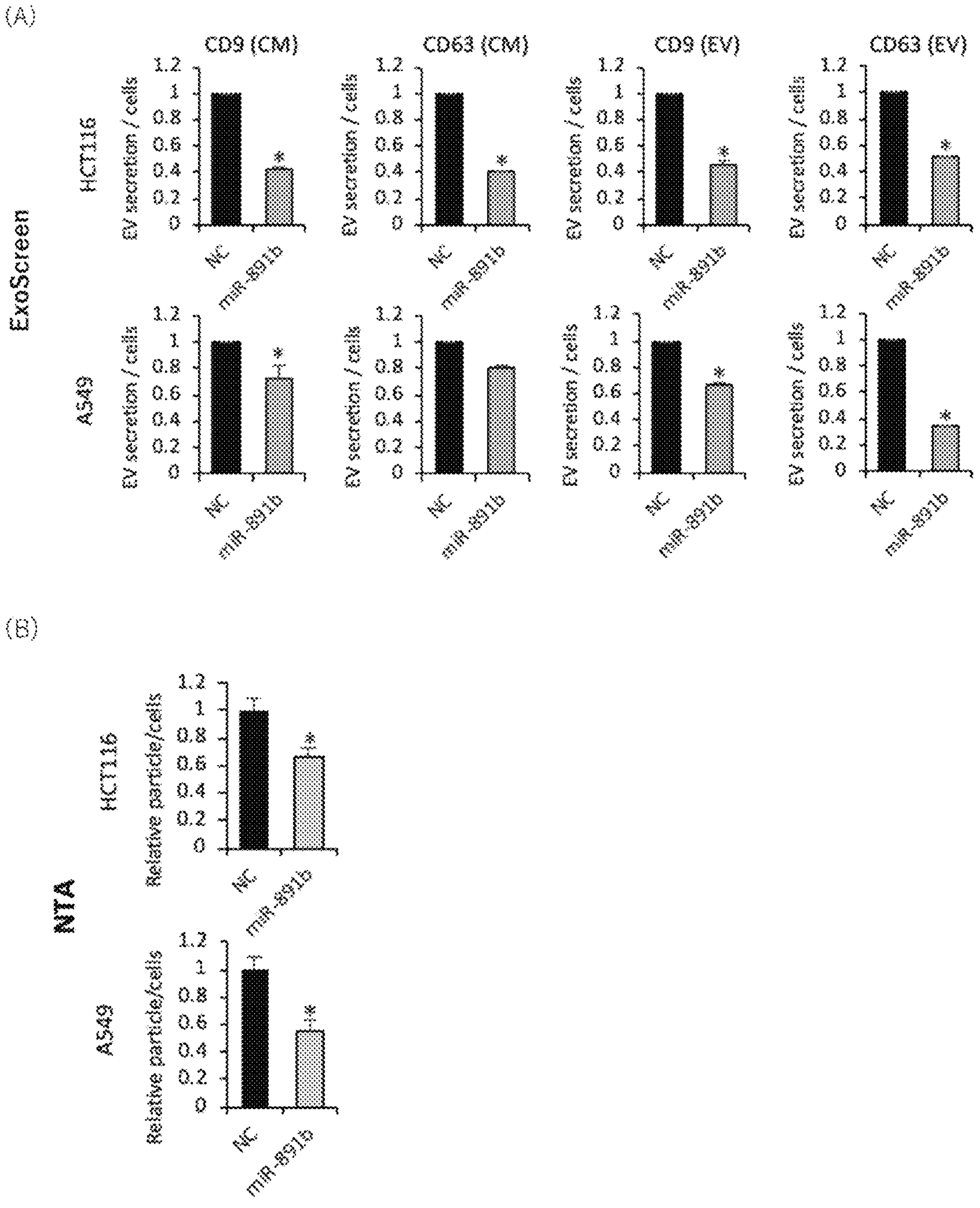
In FIG. 1, (A) shows graphs showing, regarding transformants (miR-891b) transfected with miR-891b and transformants (NC) as negative controls, the relative values of the amounts of EVs measured by the ExoScreen method; and (B) shows graphs showing the relative values of the amounts of EVs measured by the NTA method.

The extracellular vesicle (EV) secretion reducing agent of the present invention is hereinafter referred to as "EV secretion reducing agent".

In the EV secretion reducing agent of the present invention, for example, the inhibitor is an expression reducing substance that reduces expression of an enzyme protein in the serine synthesis pathway or a catalytic function reducing substance that reduces a catalytic function of an enzyme protein in the serine synthesis pathway.

In the EV secretion reducing agent of the present invention, for example, the serine synthesis pathway is a synthesis pathway that includes PSAT1.

In the EV secretion reducing agent of the present invention, for example, the inhibitor of the serine synthesis pathway is an expression reducing substance or catalytic function reducing substance for a PSAT1 protein.

In the EV secretion reducing agent of the present invention, for example, the inhibitor of the serine synthesis pathway is an expression reducing substance or catalytic function reducing substance for a PHGDH protein.

In the EV secretion reducing agent of the present invention, for example, the inhibitor of the serine synthesis pathway is an expression reducing substance or catalytic function reducing substance for a PSPH protein.

In the EV secretion reducing agent of the present invention, for example, the cell is a cancer cell.

In the EV secretion reducing agent of the present invention, for example, the cancer cell is at least one selected from the group consisting of colorectal cancer cells, lung cancer cells, melanoma cells, breast cancer cells, pancreas cancer cells, and multiple myeloma cells.

In the EV secretion reducing agent of the present invention, for example, the cell is a virus-infected cell.

In the EV secretion reducing agent of the present invention, for example, the inhibitor is a low molecular weight compound, a protein, or a peptide.

In the EV secretion reducing agent of the present invention, for example, the expression reducing substance for the enzyme protein is at least one selected from the group consisting of substances that reduce transcription from a gene encoding the enzyme protein, substances that degrade a transcription product resulting from transcription, and substances that reduce translation of the transcription product into a protein.

In the EV secretion reducing agent of the present invention, for example, the expression reducing substance is at least one nucleic acid substance selected from the group consisting of miRNAs, siRNAs, antisenses, and ribozymes.

In the EV secretion reducing agent of the present invention, for example, the expression reducing substance is an expression vector for expression of the nucleic acid substance.

In the EV secretion reducing agent of the present invention, for example, the function reducing substance for the protein is an activity inhibitory substance or an activity neutralizing substance for the enzyme protein.

In the EV secretion reducing agent of the present invention, for example, the activity neutralizing substance is an antibody or antigen-binding fragment against the protein.

In the EV secretion reducing agent of the present invention, for example, the function reducing substance is an expression vector for expression of the activity neutralizing substance.

In the EV secretion reducing method of the present invention, for example, the cell is a cancer cell.

In the EV secretion reducing method of the present invention, for example, the cancer cell is at least one selected from the group consisting of colorectal cancer cells, lung cancer cells, melanoma cells, breast cancer cells, pancreas cancer cells, and multiple myeloma cells.

In the EV secretion reducing method of the present invention, for example, the cell is a virus-infected cell.

In the EV secretion reducing method of the present invention, for example, the administration target is a human or a non-human animal.

In the EV secretion reducing method of the present invention, for example, the administration is performed in vivo or in vitro.

In the screening method for a candidate substance for the EV secretion reducing agent of the present invention, for example, the cell is a cancer cell.

In the screening method for a candidate substance for the EV secretion reducing agent of the present invention, for example, the cancer cell is at least one selected from the group consisting of colorectal cancer cells, lung cancer cells, melanoma cells, breast cancer cells, pancreas cancer cells, and multiple myeloma cells.

In the screening method for a candidate substance for the EV secretion reducing agent of the present invention, for example, the cell is a virus-infected cell.

<Extracellular Vesicle Secretion Reducing Agent>

The extracellular vesicle (EV) secretion reducing agent (hereinafter referred to as "EV secretion reducing agent") of the present invention is an agent for reducing extracellular vesicle secretion from cells. As described above, the EV secretion reducing agent of the present invention is characterized in that it contains an inhibitor of a serine synthesis pathway. The EV secretion reducing agent of the present invention is characterized in that it contains the inhibitor, and there is no particular limitation on other configurations and conditions. As to the EV secretion reducing agent of the present invention, reference can be made to the following descriptions regarding the EV secretion reducing method and the like of the present invention.

In the present invention, the inhibitor may be an expression reducing substance for an enzyme protein in the serine synthesis pathway or a catalytic function reducing substance for an enzyme protein in the serine synthesis pathway. The present invention is characterized in that it is based on the finding that the expression behavior of the serine synthesis pathway regulates EV secretion and thus the EV secretion from cells can be reduced by inhibiting the synthesis of serine, as described above. Accordingly, the type of substance used for inhibiting the serine synthesis and the method for inhibiting the serine synthesis are not limited by any means.

The inhibitor need only be capable of inhibiting the serine synthesis pathway, and there is no particular limitation on how the inhibitor inhibits the serine synthesis pathway. In other words, the inhibitor may inhibit the serine synthesis pathway by reducing the expression of an enzyme protein in the serine synthesis pathway or by reducing the catalytic function of an enzyme protein in the serine synthesis pathway. In the former case, the inhibitor is an expression reducing substance for the enzyme protein in the serine synthesis pathway, for example. In the latter case, the inhibitor is a catalytic function reducing substance for the enzyme protein in the serine synthesis pathway, for example. The EV secretion reducing agent of the present invention may contain, for example, either one of the expression reducing substance and the catalytic function reducing substance or both the expression reducing substance and the catalytic function reducing substance as the above-described inhibitor, which is an active ingredient.

The inhibitor is not limited to particular types of substances, and may be, for example, a low molecular weight compound such as a nucleic acid substance, a protein such as an antibody, or a peptide such as an antigen-binding fragment.

The expression reducing substance is not limited to particular substances, and may be, for example, a substance that reduces either transcription or translation during expression of the enzyme protein (hereinafter also referred to as “target protein”) from the gene encoding the enzyme protein (hereinafter also referred to as “target gene”). Examples of the reduction of transcription include inhibition of transcription from DNA to an mRNA precursor, inhibition of RNA processing to form a mature mRNA from an mRNA precursor, and degradation of an mRNA precursor or a mature mRNA. Examples of the reduction of translation include inhibition of translation from a mature mRNA and inhibition of modification of a translation product.

The expression reducing substance is, for example, a nucleic acid substance (hereinafter also referred to as “nucleic acid-type reducing substance”), and may be embodied as a nucleic acid substance that inhibits the expression as it is (first embodiment) or may be embodied in the form of a precursor that converts into a state capable of reducing the expression when it is in vivo, in vitro, or ex vivo (second embodiment).

The expression reducing substance of the first embodiment is, for example, an antigene substance, an antisense (antisense oligonucleotide), an RNA interference (RNAi) substance, or a ribozyme. The RNAi substance is, for example, siRNA or miRNA. The antigene substance inhibits mRNA transcription, for example. The antisense and miRNA inhibit translation from mRNA, for example. The siRNA and ribozyme degrade mRNA, for example. These expression reducing substances may target either the entire region or a partial region of the target gene, for example. As specific examples, the antisense and miRNA can be designed, for example, so as to bind to the 3' UTR region of mRNA transcribed from the target gene, and the siRNA and ribozyme can be designed, for example, so as to fully complementarily bind to a partial region of mRNA transcribed from the target gene.

The expression reducing substance of the first embodiment can be obtained by a screening method to be described below or can be designed from the sequence of the target gene, for example.

The expression reducing substance of the first embodiment may be either a single strand or a double strand, for example. There is no particular limitation on the structural units of the expression reducing substance. Examples of the structural unit include a deoxyribonucleotide backbone and a ribonucleotide backbone, each including a sugar, a base such as purine or pyrimidine, and phosphoric acid. Other examples of the structural unit include non-nucleotide backbones including a base such as pyrrolidine or piperidine. These backbones may be either modified or unmodified. The structural units may be natural structural units or unnatural, i.e., artificial structural units, for example. The expression reducing substance may be composed of the same structural units or two or more types of structural units, for example.

The expression reducing substance of the second embodiment is, as described above, the precursor, and specific examples thereof include precursors that express an expression reducing substance of the first embodiment. By administering the precursor to a target, the expression reducing substance of the first embodiment can be expressed and allowed to function in, for example, an in vivo, in vitro, or ex vivo environment.

The precursor may be in a form that includes the expression reducing substance of the first embodiment and a linker, for example. As a specific example, the precursor may be in a form in which both strands of siRNA are linked together via the linker. The precursor in such a form can generate (express) a double-stranded siRNA when, for example, the linker is removed from the precursor upon cleavage of the precursor in an in vivo, in vitro, or ex vivo environment. A specific example of the precursor is shRNA that generates siRNAs when, for example, it is cleaved.

Alternatively, the precursor may be, for example, an expression vector with the coding sequence of the expression reducing substance of the first embodiment inserted therein. Such an expression vector can cause the expression of the expression reducing substance of the first embodiment in, for example, an in vivo, in vitro, or ex vivo environment. The expression vector may have the coding sequence of, for example, the above-described precursor such as shRNA inserted therein. The expression vector is not limited to particular types of expression vectors, and may be, for example, a plasmid vector or a viral vector. Examples of the viral vector include adenovirus vectors and Sendai virus vectors.

The catalytic function reducing substance is, for example, an activity inhibitory substance that inhibits the activity of the enzyme protein or an activity neutralizing substance that neutralizes the activity of the enzyme protein.

The activity inhibitory substance is not limited to particular substances, and may be a low molecular weight compound or the like.

The activity neutralizing substance may be, for example, an antibody or antigen-binding fragment (antigen-binding peptide) against the enzyme protein (such an antibody and antigen-binding fragment are also collectively referred to as “antibody-type reducing substances” hereinafter). Since the antibody-type reducing substance can inhibit the function of the enzyme protein by, for example, binding to the enzyme protein, it is also referred to as a neutralizing antibody or a neutralizing antigen-binding fragment. The antibody-type reducing substance can also be obtained by, for example, a screening method to be described below.

The antibody may be either a monoclonal antibody or a polyclonal antibody, for example. There is no particular limitation on the isotype thereof, and examples of the isotype include IgG, IgM, and IgA. In the case where the antibody is administered to a human, it preferably is, for example, a fully human antibody, a humanized antibody, or a chimeric antibody.

The antigen-binding fragment need only be capable of, for example, recognizing a target site of the target protein and binding thereto, and examples of the antigen-binding fragment include fragments that include a complementarity-determining region (CDR) of the antibody. Specific examples of the antigen-binding fragment include fragments such as Fab, Fab', and F(ab').

The catalytic function reducing substance may be, for example, of the first embodiment in which the catalytic function reducing substance inhibits the catalytic function of the enzyme protein as is, or may be of the second embodiment in which the catalytic function reducing substance is a precursor that converts into a state capable of reducing the expression in an in vivo, in vitro, or ex vivo environment. The catalytic function reducing substance of the first embodiment is, for example, the above-described antibody-type reducing substance. The precursor of the second embodiment may be, for example, an expression vector with the coding sequence of a protein or peptide that inhibits the catalytic function of the enzyme protein inserted therein. The expression vector is not limited to particular types of expression vectors, and may be, for example, a plasmid vector or a viral vector, as with the expression vector described above in connection with the expression reducing substance.

The catalytic function reducing substance may be, for example, a substance that allows the enzyme protein to have catalytic activity and to maintain its function as a catalyst but inhibits the conditions under which the enzyme protein can exhibit the function. As a specific example, the catalytic function reducing substance may be a reducing substance that reduces a substrate that the enzyme protein needs in order to exhibit its function or a reducing substance that alters the substrate. The reduction of the substrate may be achieved by, for example, inhibiting the generation of the substrate or degrading the substrate.

The serine synthesis pathway may be, for example, a synthesis pathway (I) represented by the following formula. The EV secretion reducing agent of the present invention preferably contains, for example, an inhibitor of the serine synthesis pathway (I) that includes PSAT1. As described above, the inventors of the present invention found that the expression behavior of the serine synthesis pathway regulates the EV secretion. Specifically, the inventors found that, for example, abnormal cells such as cancer cells exhibit a higher level of EV secretion than normal cells owing to overexpression of genes and proteins encoded by these genes in the serine synthesis pathway. The inventors confirmed that an increase in EV secretion from the abnormal cells can be reduced by reducing (inhibiting) the expression of the gene encoding a protein in this serine synthesis pathway, specifically, for example, a protein in the serine synthesis pathway (I) shown below or by reducing (inhibiting) the function of such a protein, thereby achieving the present invention. Reduction of EV secretion in the present invention can also be referred to as, for example, reduction of an increase in EV secretion, and more specifically, it can also be referred to as, for example, reduction of an increase in EV secretion so as not to exceed the normal EV secretion level.

$$\text{3-PG} \xrightarrow{\text{PHGDH}} \text{P-Pyr} \xrightarrow{\text{PSAT1}} \text{P-Ser} \xrightarrow{\text{PSPH}} \text{Serine} \qquad \text{(I)}$$

PHGDH stands for D-3-phosphoglycerate dehydrogenase. Human PHGDH protein and the PHGDH gene encoding it are registered under Gene ID: 26227 in a database (the Genetic Testing Registry (GTR)). An expression reducing substance for PHGDH can be set, for example, based on the sequence of the PHGDH gene. As a catalytic function reducing substance for PHGDH, an inhibitor such as NCT-503 or CBR-5884 or a neutralizing antibody such as a PHGDH antibody can be used, for example.

PSAT1 stands for phosphoserine aminotransferase 1. Human PSAT1 protein and the PSAT1 gene encoding it are registered under Gene ID: 29968 in the database (GTR). An expression reducing substance for PSAT1 can be set, for example, based on the sequence of the PSAT1 gene, and specific examples thereof include miR-891b. As a catalytic function reducing substance for PSAT1, a neutralizing antibody such as a PSAT1 antibody can be used, for example.

PSPH stands for phosphoserine phosphatase. Human PSPH protein and the PSPH gene encoding it are registered under Gene ID: 5723 in the database (GTR). An expression reducing substance for PSPH can be set, for example, based on the sequence of the PSPH gene. As a catalytic function reducing substance for PSPH, a neutralizing antibody such as a PSPH antibody can be used, for example.

In the present invention, the inhibitor of the serine synthesis pathway may be, for example, any one of expression reducing substances and catalytic function reducing substances for a PSAT1 protein, expression reducing substances and catalytic function reducing substances for a PHGDH protein, and expression reducing substances and catalytic function reducing substances for a PSPH protein. The inhibitor of the serine synthesis pathway may include any one of them or may include two or more of them.

The EV secretion reducing agent of the present invention may contain, for example, only the above-described active ingredient or may further contain other additive ingredients. The additive ingredients are not limited to particular ingredients, and examples thereof include ingredients to be described below, which are preferably pharmacologically acceptable. The additive ingredients can be set as appropriate according to, for example, the method for administering the EV secretion reducing agent, the administration target, and the dosage form.

One example of the additive ingredient is a vehicle, for example. Examples of the vehicle include liquid media such as aqueous solvents, alcohol solvents, polyalcohol solvents, lipid solvents, and mixed solvents thereof (e.g., emulsifying solvents), lactose, and starch. Examples of the aqueous solvents include water, physiological saline, and isotonic solutions containing sodium chloride and the like. Examples of the lipid solvents include soybean oil. Other examples of the additive ingredients include: binding agents such as starch glue; disintegrants such as starch and carbonate; and lubricants such as talc and wax. The additive ingredients may also include, for example, a DDS agent for delivering the active ingredient to a target site.

In the present invention, cells to be subjected to reduction of EV secretion are not limited to particular cells, and may be cells to be subjected to reduction of extracellular vesicle secretion therefrom in order to examine the influence of the secretion or the influence of reducing the secretion. The cells may be, for example, normal cells or cells that are abnormal for an item of interest. The state of being abnormal for the item of interest is not limited to particular states. For example, when the item of interest is cancer, the abnormal cells may be cancer cells, and when the item of interest is viral infection, the abnormal cells may be virus-infected cells. Since the present invention can analyze the mechanisms of development, metastasis, treatment, and the like of cancer, the cells are preferably cancer cells. In particular, since extracellular vesicles play a role in cell-to-cell information transmission as described above, the cells are preferably cancer cells of primary cancer that may metastasize to other organs (parts of the body). The cancer cells are not limited to particular cancer cells, and examples thereof include colorectal cancer cells, lung cancer cells, melanoma cells, breast cancer cells, pancreas cancer cells, and multiple myeloma cells. Also, since the present invention can analyze the mechanism of viral infection, the cells are preferably virus-infected cells. The virus is not limited to particular types of viruses, and examples thereof include influenza viruses and coronaviruses.

In the present invention, extracellular vesicles are, for example, exosomes, microvesicles (submicroscopic vesicles), and apoptotic bodies secreted through endocytosis pathways. In particular, the extracellular vesicles in the present invention are exosomes, for example. In general, exosomes can be detected using a marker molecule such as Alix, Tsg101, CD81, CD63, CD9, or flotillin.

The method for using the EV secretion reducing agent of the present invention is not limited particular methods. For example, the EV secretion reducing agent may be added to a target to be subjected to reduction of extracellular vesicle secretion. The method for adding the EV secretion reducing agent is not limited to particular methods, and the EV secretion reducing agent may be added in vivo, in vitro, or ex vivo, for example. A target to which the EV secretion reducing agent of the present invention is to be added is, for example, cells or tissue, or may be a living organism. There is no particular limitation on the type of the cells and tissue and the part (organ) of the living organism, and examples thereof include the large intestine, lung, skin, breast, breast duct, mammary gland, pancreas, and bone marrow. The cells and tissue may be, for example, those isolated from a living organism, or may be a cell line or a culture thereof. The cells and tissue as the target may be, for example, derived from a human or a non-human animal. The living organism as the target may be, for example, a human or a non-human animal. Examples of the non-human animal include mammals such as mice, rats, rabbits, horses, sheep, cows, and camels. When the target to which the EV secretion reducing agent is to be added is derived from a non-human animal or is a non-human animal, the EV secretion reducing substance is, for example, preferably a reducing substance that relatively specifically acts on a target protein (the enzyme protein) or target gene derived from this particular non-human animal, and when the target is derived from a human or is a human, the reducing substance is, for example, preferably an reducing substance that relatively specifically acts on a target protein or target gene derived from a human.

<EV Secretion Reducing Method>

The EV secretion reducing method of the present invention is a method for reducing EV secretion from cells, and is characterized in that it includes administering the EV secretion reducing agent of the present invention to an administration target. The point of the present invention lies in using the EV secretion reducing agent of the present invention, and there is no particular limitation on other steps and conditions. As to the EV secretion reducing method of the present invention, reference can be made to the above description regarding the EV secretion reducing agent of the present invention.

When the administration target is cells, EV secretion from the cells can be reduced by, for example, adding the EV secretion reducing agent in the presence of a medium and incubating the cells. Conditions for the incubation are not limited to particular conditions, and the medium, temperature, time, humidity, and other conditions can be set according to, for example, the type of the cells.

When the administration target is tissue, EV secretion from cells that constitute the tissue can be inhibited by, for example, adding the EV secretion reducing agent in the presence of a medium and incubating the tissue. Conditions for the incubation are not limited to particular conditions. For example, the medium, temperature, time, humidity, and the like can be set according to, for example, the type and the size of the tissue.

When the administration target is a living organism, the method for administering the EV secretion reducing agent is not limited to particular methods, and may be parenteral administration, oral administration, intravenous administration, or the like. Administration conditions are not limited to particular conditions and can be determined as appropriate according to, for example, the type of the living organism and the type of the organ as the administration target.

When the administration method is parenteral administration, an administration site may be, for example, a target organ, i.e., an organ that includes cells to be subjected to reduction of EV secretion (such an organ is also referred to as "target site"), or a site from which the inhibitor as the active ingredient of the EV secretion reducing agent can be delivered to the target site. As a specific example, when the target cells are, for example, large intestinal cells, the administration site may be the large intestine as the target site or a site from which the inhibitor can be delivered to the large intestine. When the target cells are, for example, lung cells, the administration site may be the lung as the target site, or a site from which the inhibitor can delivered to the lung. The same applies to other organs. Examples of the parenteral administration method include injection to an affected area, intravenous injection, subcutaneous injection, intradermal injection, intravenous infusion, and transdermal administration. The form of the EV secretion reducing agent is not limited to particular forms, and can be set as appropriate according to the administration method and the like, as described above. As to the form of the EV secretion reducing agent, reference can be made to the above description thereon.

In the case of parenteral administration, the dosage form is not limited to particular forms, and can be determined as appropriate according to the administration method. For example, the EV secretion reducing agent may be in the form of liquid, cream, or gel, and can be prepared by mixing the inhibitor with a medium. Of the above-described examples of the medium, the aqueous solvent is, for example, physiological saline or an isotonic solution, the lipid solvent is, for example, soybean oil, and the emulsifying solvent is, for example, a mixture thereof. Such a parenteral administration agent may further contain, for example, alcohol, polyalcohol, and/or a surfactant. Also, the parenteral administration agent may contain a DDS agent for effectively delivering the inhibitor to a target site from a site other than the target site. In particular, in order to effectively deliver the inhibitor to, for example, cancer cells in tissue as the target site, the parenteral administration agent may contain, for example, a DDS agent that specifically recognizes the cancer cells.

In the case of oral administration, the dosage form of an oral administration agent is not limited to particular forms, and examples thereof include tablets, pills, granules, powder medicines, capsules, and syrups. The oral administration agent may contain, for example, a diluent, a vehicle, and/or a carrier. The oral administration agent may also contain, for example, a DDS agent for effectively delivering the inhibitor to the target site. In particular, in order to effectively deliver the inhibitor to, for example, cancer cells in tissue as the target site, the oral administration agent may contain, for example, a DDS agent that specifically recognizes the cancer cells.

In administration to a living organism, the administration conditions of the EV secretion reducing agent of the present invention can be determined as appropriate according to, for example, the age, the body weight, the type of organ as the administration target, and the sex.

The inventors of the present invention have reported, as the mechanism of cancer metastasis, that extracellular vesicles are secreted from cancer cells of primary cancer and the cancer metastasis is caused via cell-to-cell information transmission mediated by the extracellular vesicles. As described above, by administering the EV secretion reducing agent of the present invention to a target site (cancerous organ) of a patient affected by cancer, extracellular vesicle secretion from cancer cells in the target site is reduced, whereby progression of cancer and metastasis of cancer to other organs can be reduced. Accordingly, the EV secretion reducing agent of the present invention can also be used as a therapeutic agent for cancer, for example. The term "treatment" as used in the present specification encompasses, for example, not only what are called practices to alleviate the progression of cancer, to treat cancer, and the like but also preventive practice to prevent the onset or recurrence of cancer. The EV secretion reducing agent of the present invention may be used for, for example, any one of the above-described purposes or two or more of the above-described purposes.

In this case, in the administration to a living organism, the administration conditions of the EV secretion reducing agent of the present invention can be determined as appropriate according to, for example, in addition to the items given above as examples, the type of cancer (e.g., colorectal cancer, lung cancer, melanoma, breast cancer, pancreas cancer, and multiple myeloma) and the degree of progression of cancer. The living organism may be, for example, a subject affected by cancer from the viewpoint of treating the cancer, or may be a subject not affected by cancer or a subject who may or may not affected by cancer from the viewpoint of preventing the cancer.

It is to be noted, however, that the intended use of the EV secretion reducing agent of the present invention is not limited to those given above as examples. In recent years, for example, it has been reported that EVs such as exosomes are involved in cell-to-cell communication in the body. Specific examples thereof include transmission of a virus infecting a subject (for example, an influenza virus or a coronavirus) in the body. Accordingly, the EV secretion reducing agent of the present invention reduces, for example, viral transmission through reduction of EV secretion, thereby enabling inhibition of the spread of viral infection in the body.

EVs whose secretion is reduced by the EV secretion reducing agent of the present invention are known to play a role in cell-to-cell information transmission by, for example, transferring an information cargo in a certain cell to another cell, as described above. Accordingly, the EV secretion reducing agent of the present invention also can be referred to as, for example, a cell-to-cell information transmission reducing agent, and the EV secretion reducing method of the present invention also can be referred to as a cell-to-cell information transmission reducing method.

<Screening Method>

The screening method of the present invention is a screening method for a candidate substance for an EV secretion reducing agent for reducing EV secretion from cells, and the screening method is characterized in that it includes selecting, out of test substances, an inhibitory substance that inhibits a serine synthesis pathway as a candidate substance that reduces extracellular vesicle secretion from cells. The cells are not limited to particular types of cells and are as described above. Examples of the cells include cancer cells. As described above, examples of the cancer cells include colorectal cancer cells, lung cancer cells, melanoma cells, breast cancer cells, pancreas cancer cells, and multiple myeloma cells.

In the case where a candidate substance for the expression reducing substance is selected through screening, the screening method of the present invention includes, for example: in an expression system for expressing the above-described enzyme protein (target protein) from the above-described gene (target gene) encoding the enzyme protein, expressing the target protein in the presence of each of the test substances; detecting expression of the target protein in the expression system; and selecting, as the candidate substance, a test substance in the presence of which the expression level of the target protein is relatively low as compared with the expression level of the target protein in a control expression system without the test substance.

In the case where the catalytic function reducing substance is selected through screening, the screening method of the present invention includes, for example: bringing each of the test substances into contact with the above-described enzyme protein (target protein); detecting the catalytic activity of the target protein; and selecting, as the candidate substance, a test substance that causes the enzyme protein to exhibit relatively low catalytic activity as compared with the enzyme protein in a control system without the test substance.

In the case where the activity neutralizing substance is selected through screening as a candidate substance for the catalytic function reducing substance, the screening method of the present invention includes, for example: bringing each of the test substances into contact with the above-described enzyme protein (target protein); detecting binding of the target protein and the test substance; and selecting, as the candidate substance, a test substance that has bound to the target protein.

<Use>

The present invention relates to the above-described inhibitor for use in reduction of extracellular vesicle secretion from cells. As to the above-described reducing substances, reference can be made to the above description regarding the EV secretion reducing agent of the present invention and the EV secretion reducing method of the present invention.

EXAMPLES

Next, examples of the present invention will be described. It is to be noted, however, that the present invention is by no means limited by the following examples. Commercially available reagents were used in accordance with their protocols, unless otherwise stated.

(Cells)

A human colon adenocarcinoma cell line HCT116 (ATCC CCL-247) was used as colorectal cancer cells, and an adenocarcinomic human alveolar basal epithelial cell line A549 (ATCC CCL-185) was used as lung cancer cells. A human melanoma cell line A375 (ATCC CRL-1619) was used as melanoma cells. A human breast cancer cell line MM231 (ATCC HTB-26) was used as breast cancer cells. A human pancreatic adenocarcinoma cell line Panc-1 (ATCC CRL-1469) was used as pancreas cancer cells. A human multiple myeloma cell line RPMI 8226 (ATCC CCL-155) was used as human multiple myeloma cells.

(Nucleic Acid Molecules)

miR-891b (also referred to as "miR-891b mimic", SEQ ID NO: 1: GCAACUUACCUGAGUCAUUGA) (Product No. 4464066, Ambion) was used as a nucleic acid molecule miRNA, and miRNA Mimic Negative Control #1 (4464058) (Ambion) was used as a negative control nucleic acid molecule miRNA. siPSAT1 (Product No. siGENOME SMART pool siRNA M-010398, Dharmacon) was used as a nucleic acid molecule siRNA, and ALL STAR Negative Control siRNA (SI03650318) (Qiagen) was used as a negative control nucleic acid molecule siRNA.

(Cell Culture)

The medium used for MM231 was an RPMI complete medium obtained by adding 10% heat-inactivated fetal bovine serum (FBS) and an antibiotic-antimycotic solution (Gibco) to an RPMI 1640 medium (Gibco). The medium used for HCT116 was a Maccoy 5A complete medium obtained by adding 10% heat-inactivated FBS and an antibiotic-antimycotic agent to a Maccoy 5A medium. The medium used for each of the other types of cells was a DMEM complete medium obtained by adding 10% heat-inactivated FBS and an antibiotic-antimycotic agent to a DMEM medium (Gibco). The culture conditions were set to 37° C., 5% carbon dioxide, and 95% relative humidity (RH). About 100,000 cells were seeded in 18 mL of each of the above-described complete media and incubated for 3 to 4 days. Cells that had undergone less than 20 passages were used.

(Collection of Secreted EVs)

The cultured cancer cells were washed with phosphate buffered saline (PBS), and the medium was replaced with advanced RPMI or advanced DMEM containing the above-described antibiotic-antimycotic agent and 2 mmol/L L-glutamine (Gibco). The adjusted culture solution after the replacement was centrifuged at 2,000×g for 10 minutes to remove the cells, and the supernatant obtained was filtered through a 0.22 μm filter (Millipore). The resulting filtrate was centrifuged at 110,000×g for 70 minutes, whereby pellets containing concentrated EVs were obtained. The pellets were washed with 11 mL of PBS, further ultracentrifuged at 110,000×g for 70 minutes, and collected again.

(ExoScreen Method)

EV detection was performed using an AlphaLISA reagent (Perkin Elmer) composed of AlphaScreen streptavidin-coated donor beads (6760002), AlphaLISA unconjugated acceptor beads (6062011), and an AlphaLISA universal buffer (AL001F), a 96-well half-area white plate (6005560, Perkin Elmer), and a detection device EnSpire Alpha 2300 Mutilabel plate reader (Perkin Elmer). Specifically, the EV detection was performed as follows. Each well of the plate was filled with 5 μL of EVs or 10 μL of CM (cell culture supernatant), 10 μL of a 5 nmol/L biotinylated antibody solution prepared using the above-described buffer, and 10 μL of 50 μg/mL AlphaLISA acceptor bead-conjugated antibody. For detection of CD9/CD9 double-positive EVs, a biotinylated anti-human CD9 antibody and an anti-human CD9 antibody conjugated with AlphaLISA acceptor beads were used. For detection of CD9/CD63 double-positive EVs, a biotinylated anti-human CD9 antibody and an anti-human CD63 antibody conjugated with AlphaLISA acceptor beads were used. For detection of CD63/CD63 double-positive EVs, a biotinylated anti-human CD63 antibody and an anti-human CD63 antibody conjugated with AlphaLISA acceptor beads were used. The plate was incubated at 37° C. for 1 hour, and then, 25 μL of 80 μg/mL AlphaScreen streptavidin-coated donor beads were added thereto. The plate was incubated at 37° C. for another 30 minutes in the dark. Next, luminescence in the wells of the plate was measured using the detection device with the excitation wavelength set to 680 nm and the emission detection wavelength set to 615 nm. The antibodies used were both commercially available products, namely, a mouse monoclonal anti-human CD9 (Clone 12A12) and a CD63 antibody (Clone 8A12) (both available from Cosmo Bio).

(Analysis of EVs by Nanoparticle Tracking Analysis NTA)

The secreted EVs were collected and then suspended in PBS. Further, a series of diluted solutions were prepared using PBS and subjected to NanoSight particle tracking analysis (LM10, software ver. 2.03). In the above-described particle tracking, at least five 60-second videos were taken for each sample with the camera level set to 14. Analysis settings were optimized and kept constant between the samples. An EV concentration was calculated as particles/cells in the culture solution, whereby a net EV secretion rate was obtained. The results of EV measurement by the ExoScreen method correlated with the results of EV measurement by the NTA analysis. This confirmed that the ExoScreen method is capable of measuring the amount of secreted EVs.

(Transient Transfection Assay)

In a 6-well plate, 2 mL of the cancer cell suspension was seeded at $1.0\times10^5$ cells/well and incubated for 24 hours. Thereafter, 10 nmol/L of the intended nucleic acid molecules were added thereto, and the cells were transfected with the nucleic acid molecules using a transfection reagent (product name: DharmaFECT Transfection Reagent 1). The nucleic acid molecules used were the above-described miRNA and the above-described siRNA. After the incubation for 24 hours, the medium was replaced with the above-described advanced RPMI 1640 medium or advanced DMEM medium containing the antibiotic-antimycotic agent and 2 mmol/L-glutamine (Gibco). 48 hours after the replacement, total RNA was extracted, and the expression of the gene of interest was measured by qPCR.

(RNA Extraction and qPCR Analysis)

The total RNA was extracted from the cultured cells using commercially available reagents (trade name: QIAzol, trade name: miRNeasy Mini Kit, Qiagen). Reverse transcription reactions were caused using a commercially available kit (trade name: High-Capacity cDNA Reverse Transcription Kit, Applied Biosystems) and random hexamer primers. Real-time PCR analysis was performed using commercial kits (trade name: StepOne Plus, trade name: TaqMan Universal PCR MasterMix, Thermo Fisher Scientific). mRNA expression was normalized using β-actin. As a probe for PSAT1, a TaqMan probe (Applied Biosystems) was used.

Unless otherwise stated, data presented in the examples were each expressed as the mean value±the standard error. The statistical significance was determined using a Student's t-test. In dot plots, each bar indicates the median and the interquartile range, and the statistical significance was determined by a Student's t-test. $P<0.05$ was considered as statistically significant.

* $P<0.05$, ** $P<0.01$.

Example A

Example A1

The present example identified target genes involved in regulation of EV secretion in colorectal cancer and lung cancer.

(1) Detection of EVs Secreted from Cancer Cells

Colorectal cancer cells HCT116 and lung cancer cells A549 were each transfected with miR-891b. Culture supernatants (CM) of the resulting transformants (miR-891b) and EV fractions containing EVs secreted from the transformants (miR-891b) were collected. Then, according to the ExoScreen method described above, the amounts of the secreted EVs were measured by measuring the signal intensities. Also, the amounts of the secreted EVs measured for the respective transformants were confirmed by the NTA analysis. As a negative control, regarding a transformant (NC) obtained by transfecting the cells with miR-891b miRNA Mimic Negative Control #1, the amount of secreted EVs was measured in the same manner. Then, assuming that the amount of secreted EVs in the transformant (NC) was 1, the relative values (n=3) of the amounts of secreted EVs in the transformants (miR-891b) were determined.

The results obtained are shown in FIG. 1. In FIG. 1, (A) shows graphs showing the relative values of the amounts of secreted EVs measured by the ExoScreen method, and (B) shows graphs showing the relative values of the amounts of secreted EVs measured by the NTA method. As can be seen from (A) in FIG. 1, in the transformants (miR-891b) obtained by transfecting the colorectal cancer cells HCT116 and the lung cancer cells A549 with miR-891b, the amounts of the secreted EVs observed in both the CMs and the EV fractions were significantly lower than those observed in the transformants (NC). Also, as can be seen from (B) in FIG. 1, similar results were obtained also by the NTA method. These results demonstrate that miR-891b reduces EV secretion in colorectal cancer cells and lung cancer cells.

(2) Target Gene of miR-891b

Figure 2:
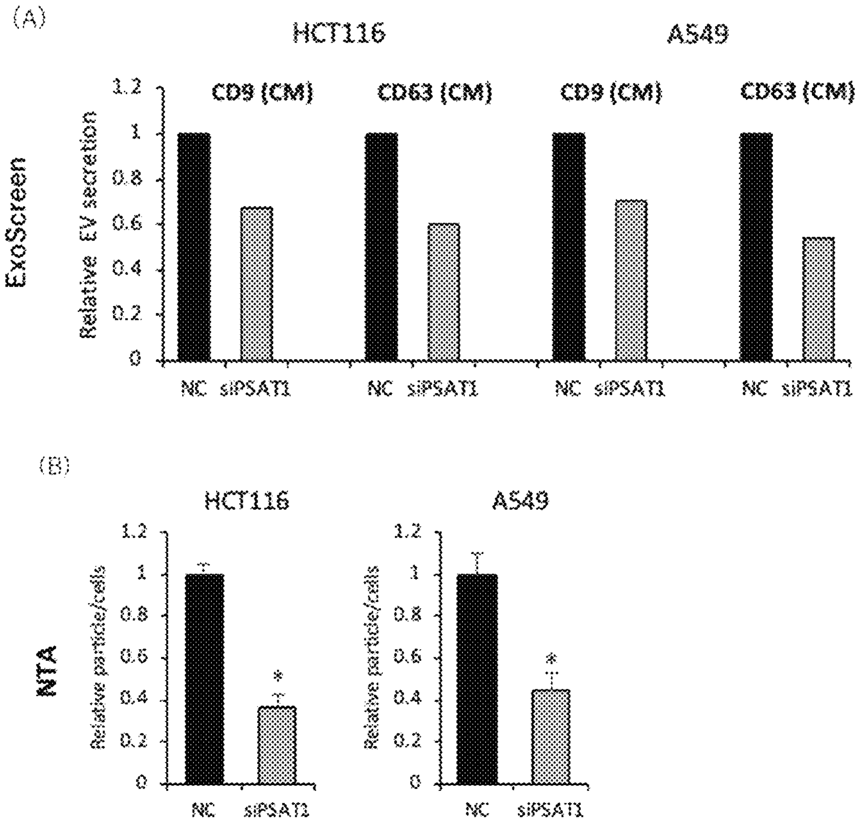
In FIG. 2, (A) shows graphs showing, regarding transformants (siPSAT1) transfected with siPSAT1 and transformants (NC) as negative controls, the relative values of the amounts of EVs measured by the ExoScreen method; and (B) shows graphs showing the relative values of the amounts of EVs measured by the NTA method.

In the above item (1), EV secretion was reduced by transfection with miR-891b. The inventors of the present invention conducted further in-depth studies and found that the PSAT1 gene is a target gene whose expression is reduced by miR-891b. To support this finding, colorectal cancer cells HCT116 and lung cancer cells A549 were transfected with siRNA (siPSAT1) for reducing the expression of the PSAT1 gene, and the amounts of secreted EVs were measured by the ExoScreen method and the NTA method. Also, as negative controls, the amounts of secreted EVs were measured in the same manner, except that these cancer cells were transfected with ALL STAR negative control siRNA. The results obtained are shown in FIG. 2. In FIG. 2, (A) shows graphs showing the relative values of the amounts of secreted EVs measured by the ExoScreen method, and (B) shows graphs showing the relative values of the amounts of secreted EVs measured by the NTA method.

As can be seen from (A) in FIG. 2, in the transformants (siPSAT1) obtained by transfecting the colorectal cancer cells HCT116 and the lung cancer cells A549 with siPSAT1, the amounts of the secreted EVs observed in both the CMs and the EV fractions were significantly lower than those observed in the transformants (NC). Also, as can be seen from (B) in FIG. 2, similar results were obtained also by the NTA method. The fact that the downregulation of the PSAT1 gene with siPSAT1 reduced the EV secretion and also the results in the above item (1) demonstrate that the PSAT1 gene is the target gene of miR-891b.

(3) Confirmation of Target Gene

The following test was conducted to examine whether the PSAT1 gene described in the item (2) is a direct target gene of miR-891b.

Figure 3:
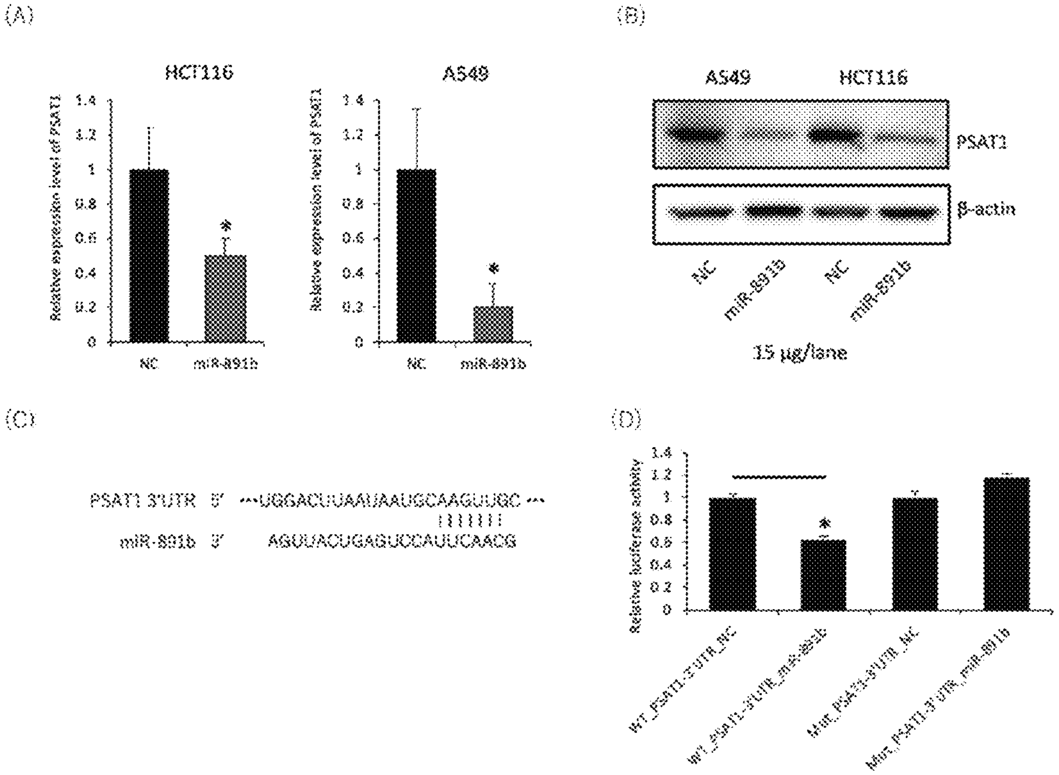
In FIG. 3, (A) shows graphs showing, regarding the above-described transformants (miR-891b) and the above-described transformants (NC), the relative values of PSAT1 gene expression levels, (B) shows Western blot pictures indicating the expression of a PSAT1 protein, (C) shows the relationship between the 3' UTR of the PSAT1 gene and miR-891b, and (D) shows a graph showing the PSAT1 expression levels in transformants transfected with the PSAT1 gene and miR-891b.

First, expression of the PSAT1 gene was detected in the above-described transformants (miR-891b) and the control transformants (NC) therefor. Then, assuming that the expression levels in the transformants (NC) were 1, the relative values of the expression levels in the respective transformants (miR-891b) were determined. The results obtained are shown in (A) of FIG. 3. In FIG. 3, (A) shows graphs showing the relative values of the PSAT1 gene expression levels. Also, for the transformants (miR-891b) and the control transformants (NC), the PSAT1 protein expression was detected by Western blotting. As a control, 8-actin was also detected. The results obtained are shown in (B) in FIG. 3. In FIG. 3, (B) shows Western blot pictures indicating the PSAT1 protein expression.

Next, as can be seen from (C) in FIG. 3, miR-891b has a sequence that perfectly matches a region consisting of seven contiguous bases in the 3' UTR of the human PSAT1 mRNA (SEQ ID NO: 2: UGGACUUAAUAAUGCAAGUUGC is a partial region of the 3' UTR). Thus, the effect of miR-891b was examined using the wild-type PSAT1 gene in which the above-described 7-base region in the 3' UTR is the wild-type sequence (SEQ ID NO: 3: AAGTTGC) and a mutant-type PSAT1 gene in which the above-described 7-base region in the 3' UTR is a mutated sequence (SEQ ID NO: 4: TTCAACG). Specifically, the following experiment was performed. The wild-type PSAT1 gene or the mutant-type PSAT1 gene was subcloned into a plasmid vector psi-CHECK2, and human embryonic kidney cells (HEK293 cells) were transfected with this recombinant vector together with miR-891b or the negative control miRNA using Lipofectamine 3000. 48 hours after the transfection, the luciferase activity of the transformants was quantified using a plate reader according to the operating procedure of a Dual-Luciferase Reporter Assay System.

The results obtained are shown in (D) of FIG. 3. In FIG. 3, (D) shows a graph showing the PSAT1 expression levels as the relative luciferase activity.

As can be seen from (D) in FIG. 3, transfection with miR-891b reduced the PSAT1 gene expression and the PSAT1 protein expression. Furthermore, transfection with miR-891b significantly reduced the PSAT1 expression level in the case where the wild-type PSAT1 in which the sequence of the region recognized by miR-891b is the wild-type sequence was used, whereas transfection with miR-891b did not reduce the PSAT1 expression level in the case where the recognition region of miR-891b had a mutated sequence. From these results, it was found that miR-891b cleaves PSAT1 upon recognition of the 3' UTR of PSAT1. In other words, these results attest that the PSAT1 gene is a direct target of miR-891b.

Example A2

The present example examined whether reducing the expression of the PSAT1 gene reduces EV secretion from various types of cancer cells.

Figure 4:
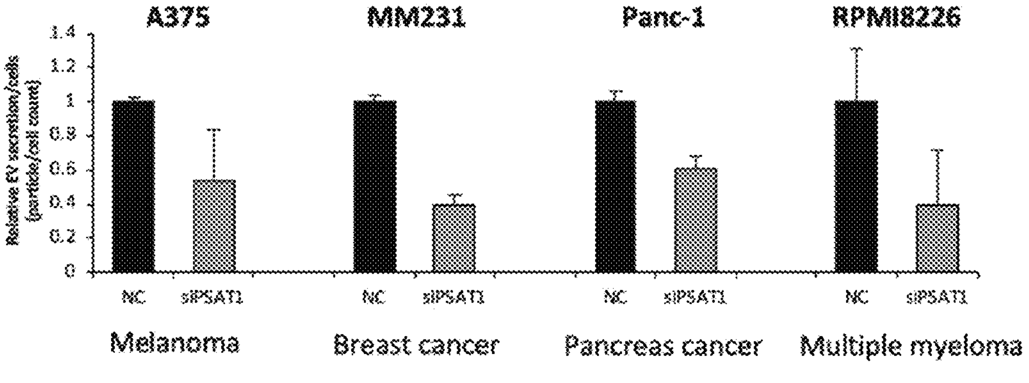
FIG. 4 shows a graph showing, regarding transformants (siPSAT1) obtained by transfecting various types of cancer cells with siPSAT1 and transformants (NC) as negative controls, the relative values of the amounts of secreted EVs measured by the NTA method.

Transfection with siRNA (siPSAT1) and measurement of the amount of secreted EVs by the nanoparticle tracking analysis (NTA) method were performed in the same manner as in the item (2) of Example A1, except that melanoma cells A375, breast cancer cells MM231, pancreas cancer cells Panc-1, and multiple myeloma cells RPMI8226 were used. The results obtained are shown in FIG. 4. FIG. 4 shows a graph showing the relative values of the amounts of secreted EVs measured by the NTA method.

As can be seen from FIG. 4, in a transformant (siPSAT1) obtained by transfecting each type of the cancer cells with siPSAT1, the amount of the secreted EVs was significantly lower than that observed in the transformant (NC) as the negative control therefor. From these results, it was found that reducing the expression of PSAT1 can reduce EV secretion not only in colorectal cancer cells and lung cancer cells but also in various types of other cancer cells. From these results, it can be said that EV secretion from various types of cancer cells can be reduced by reducing the expression of PSAT1, thus enabling treatment of these cancers and prevention of metastasis of these cancers to other organs.

Example A3

Colorectal cancer cells HCT116 and lung cancer cells A549 were transfected with siRNA (siPSAT1) in the same manner as in the item (2) in Example A1, and EV biogenesis after PSAT1 silencing was examined. For the respective silenced transformants, CD63 and PSAT1 were examined by immunofluorescence. As a result, accumulation of CD63 as an EV marker was observed in cytoplasm after the PSAT1 silencing. Also, when these cells were transfected with miR-891b, accumulation of CD63 was observed, as with the above-described case. These results confirmed that, although the EV production itself is maintained even when the PSAT1 expression is reduced, the produced EVs accumulate in cytoplasm and reduce the secretion of the EVs from the cells to the outside.

Figure 5:
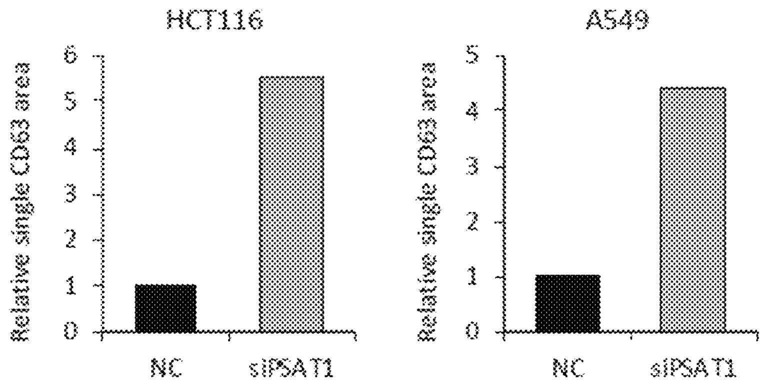
FIG. 5 shows graphs showing, regarding transformants (siPSAT1) obtained by transfecting cancer cells with siPSAT1 and transformants (NC) as negative controls, the relative amounts of CD63-positive EVs in the cells.

Further, coimmunostaining of the EV marker CD63 and also an early endosome marker EEA1 or a late endosome marker Rab7 was conducted for the PSAT1-silenced transformants. As a result, no overlap was observed between EEA1 and CD63 in either the PSAT1-silenced transformants or the negative control transformants. On the other hand, an almost complete overlap was observed between CD63 and Rab7 in the negative control transformants, whereas a slight overlap was observed between CD63 and Rab7 in the PSAT1-silenced transformants. On this account, the CD63 single-positive area was measured based on the intensity. The results obtained are shown in FIG. 5. As can be seen from FIG. 5, in both the HCT116 and A549, the PSAT1 silencing greatly increased the CD63 single-positive area. This confirmed that EVs had accumulated in the cells. These results suggest the possibility that PSAT1 may play a role in EV secretion during the synthesis of late endosome.

Example B

Example A described above confirmed that PSAT1 is involved in EV secretion and that EV secretion can be reduced by reducing the expression of PSAT1. Since PSAT1 is an enzyme protein in the serine synthesis pathway, it was speculated that the serine synthesis pathway is involved in EV secretion and inhibiting the serine synthesis pathway, i.e., inhibiting serine synthesis can reduce the EV secretion. Thus, Example B examined whether EV secretion can be reduced by inhibiting any of the steps in the serine synthesis pathway other than PSAT1.

Example B1

Ordinary DMEM media contain serine. Accordingly, a serine-deficient medium was used to examine the effect brought about by adding serine on the EV secretion.

A serum-free serine-containing MEM medium containing 1× insulin, transferrin, selenium solution (100×ITS-G), 1×MEM vitamin solution, and serine (4 mmol/L) and a serum-free serine-deficient MEM medium having the same composition as this serum-free serine-containing MEM medium except that serine was not contained therein were used in the present example. Colorectal cancer cells HCT116 and lung cancer cells A549 were each seeded in a 96-well plate at $5\times10^3$ cells/well and in a 6-well plate at $1.5\times10^5$ cells/well (Day 0), and incubated for 24 hours in a medium (DMEM containing 10% FBS and 1× antibiotic-antimycotic). After the incubation (Day 1), each type of cells were transfected with siRNA (siPSAT1) or ALL STAR negative control siRNA (NC) and incubated for another 24 hours. After the incubation (Day 2), the medium in the wells was replaced with the above-described serine-deficient MEM medium or serine-containing MEM medium. After another 48 hours of incubation (Day 4), the 96-well plate was used in the ExoScreen method and the post-culture medium was collected from the 6-well plate. Secreted EVs were collected from the collected medium and then subjected to the NTA.

As a result, the growth of the PSAT1-silenced transformants in the serine-deficient MEM medium was slower than the growth thereof in the serine-containing MEM medium.

Figure 6:
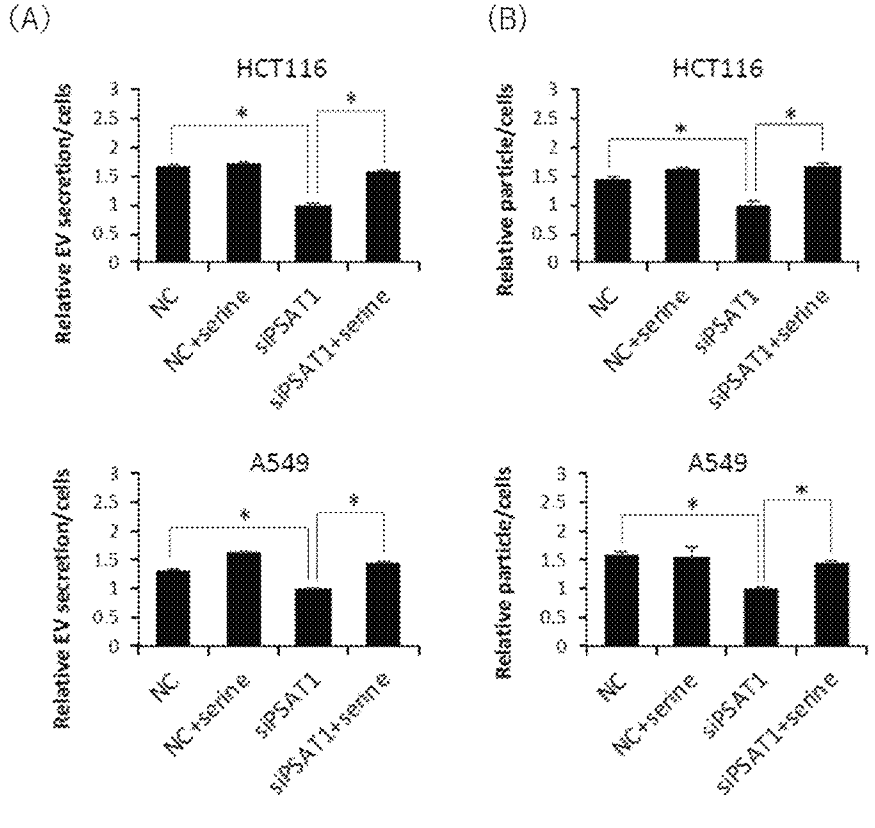
FIG. 6 shows results obtained when transformants (siPSAT1) obtained by transfecting cancer cells with siPSAT1 and transformants (NC) as negative controls were cultured in a serine-deficient medium or a serine-containing medium. (A) shows graphs showing the relative values of the amounts of secreted EVs measured by the ExoScreen method, and (B) shows graphs showing the relative values of the amounts of secreted EVs measured by the NTA method.

The results of the measurement by the ExoScreen method and the NTA are shown in FIG. 6. In the ExoScreen method, the amount of secreted EVs was determined as a relative value calculated assuming that the measurement result for the transformant transfected with siRNA (siPSAT1) was 1. In the NTA, the amount of secreted EVs was determined as a relative value calculated assuming that the amount of secreted EVs in the transformant transfected with siRNA (siPSAT1) was 1. In FIG. 6, (A) shows graphs showing the relative values of the amounts of secreted EVs measured by the ExoScreen method, and (B) shows graphs showing the relative values of the amounts of secreted EVs measured by the NTA method.

As can be seen from FIG. 6, in the PSAT1-unsilenced negative controls (NC), the results of using the serine-deficient MEM medium and the results of using the serine-deficient MEM medium were approximately the same. In contrast, when the transformants transfected with siRNA (siPSAT1) were cultured in the serine-deficient MEM medium, the amounts of secreted EVs were smaller than those in the negative control transformants (NC). Also, when the transformants transfected with siRNA (siPSAT1) were cultured using the serine-containing MEM medium (i.e., when serine was added to the transformants), the amounts of secreted EVs were significantly increased as compared with the case where they were cultured using the serine-deficient MEM medium and were roughly equivalent to those in the negative controls (NC). From these results, it was found that serine synthesis is involved in EV secretion and that EV secretion can be reduced by inhibiting the serine synthesis.

Example B2

An inhibitor of the serine synthesis pathway was used to examine the effect thereof on EV secretion.

As the inhibitor, an inhibitor NCT-503 of an enzyme protein (PHGDH) in the serine synthesis pathway was used.

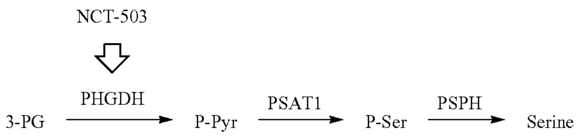

Specifically, the test was performed in the following manner. Colorectal cancer cells HCT116 and lung cancer cells A549 were each seeded in a 6-well plate at $1.5\times10^5$ cells/well (Day 0), and incubated for 24 hours in a medium (DMEM with 10% FBS, 1× anti-anti medium). After the incubation (Day 1), the above-described medium was removed, and thereafter, a serine-deficient medium and an inhibitor solution were added to the wells. The inhibitor solution was prepared by dissolving NCT-503 in DMSO, and the concentration of the inhibitor per well was set to 2.5 μmol/L. Then, after another 48 hours of incubation (Day 3), the medium in the wells was collected and the cells in the wells were counted. As negative controls (NC), the test was performed in the same manner, except that DMSO was added instead of the inhibitor solution.

Figure 7:
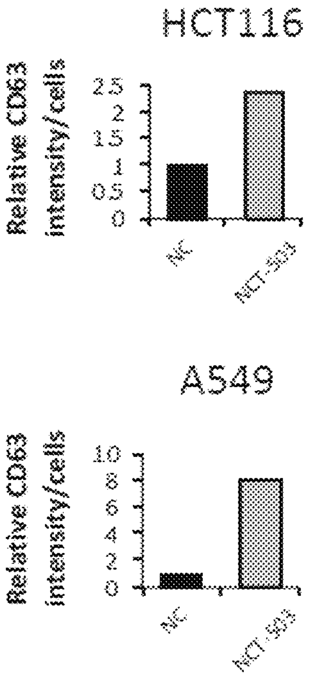
FIG. 7 shows graphs showing the relative amounts of CD63-positive EVs in cells.
Figure 8:
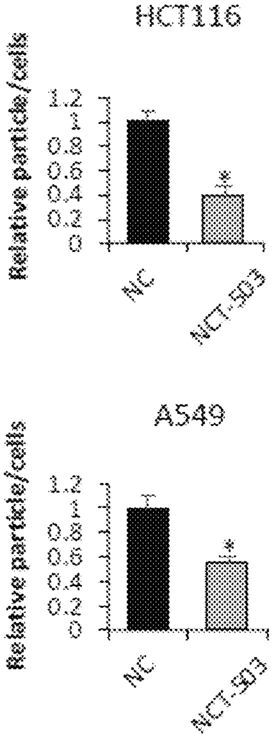
FIG. 8 shows graphs showing, regarding cancer cells cultured in the presence of an inhibitor of the serine synthesis, the relative values of the amounts of secreted EVs measured by the NTA method.

EVs accumulated in the cells were analyzed in the following manner. Specifically, the collected cells were immunostained, the CD63 single-positive area was measured based on the fluorescence intensity, and the fluorescence intensity measured in the area was divided by the number of nuclei to determine the amount of EVs accumulated in each cell. The results obtained are shown in FIG. 7. On the other hand, secreted EVs were collected from the collected medium and then subjected to the NTA. In the NTA, the amount of secreted EVs was determined as a relative value calculated assuming that the amount of the secreted EVs in the negative control was 1. The results thereof are shown in FIG. 8.

First, as a result of immunofluorescence observation, intracellular accumulation of CD63-positive EVs resulting from the coexistence of the cancer cells with the inhibitor was confirmed, as with the results regarding the PSAT1-silenced transformants in Example A3 above. These results agree with the results shown in FIG. 7. That is to say, also in FIG. 7, the amounts of EVs in the cells with the coexisting inhibitor were larger than those in NCs, and this confirmed that EVs had accumulated in the cells and the secretion of these EVs was inhibited. Correspondingly, as can be seen from FIG. 8, the amounts of EVs in the media of the cells with the coexisting inhibitor were smaller than those in NCs, and this indicates that EV secretion from the cells was inhibited. Also from these results, it was found that EV secretion can be reduced by inhibiting serine synthesis.

Example C

Using various types of cancer cells, the regulation of EV secretion by serine synthesis was examined. Although the present example used PSAT1 silencing to inhibit the serine synthesis pathway, inhibition of the serine synthesis pathway is not limited to PSAT1 silencing, and it had been confirmed that any inhibition of the serine synthesis can similarly reduce EV secretion, as described above.

Cells used in the present examples were colorectal cancer cell lines (HCT15, COLO201, COLO205, and HT-29), normal colorectal fibroblast cells (CCD-18co), lung cancer cell lines (A427, H1650, and 112228), and normal lung epithelial cells. Total RNAs were prepared from the respective types of cells and the expression levels of PSAT1 were examined. As a result, it was found that, in both the large intestinal cells and the lung cells, the expression levels of PSAT1 in the cancer cells were significantly higher than those in the normal cells. Not only for the colorectal cancer cells and the lung cancer cells but also for cells of ovarian cancer, breast cancer, melanoma, head and neck cancer, multiple myeloma, and pancreas cancer, the present example confirmed that the expression levels of PSAT1 in cancer cells were significantly higher than those in normal cells in the same manner as in the above. The expression level of PSAT1 in lung cancer patients highly correlated with the survival rate. Specifically, the higher the expression level, the lower the survival rate.

Figure 9:
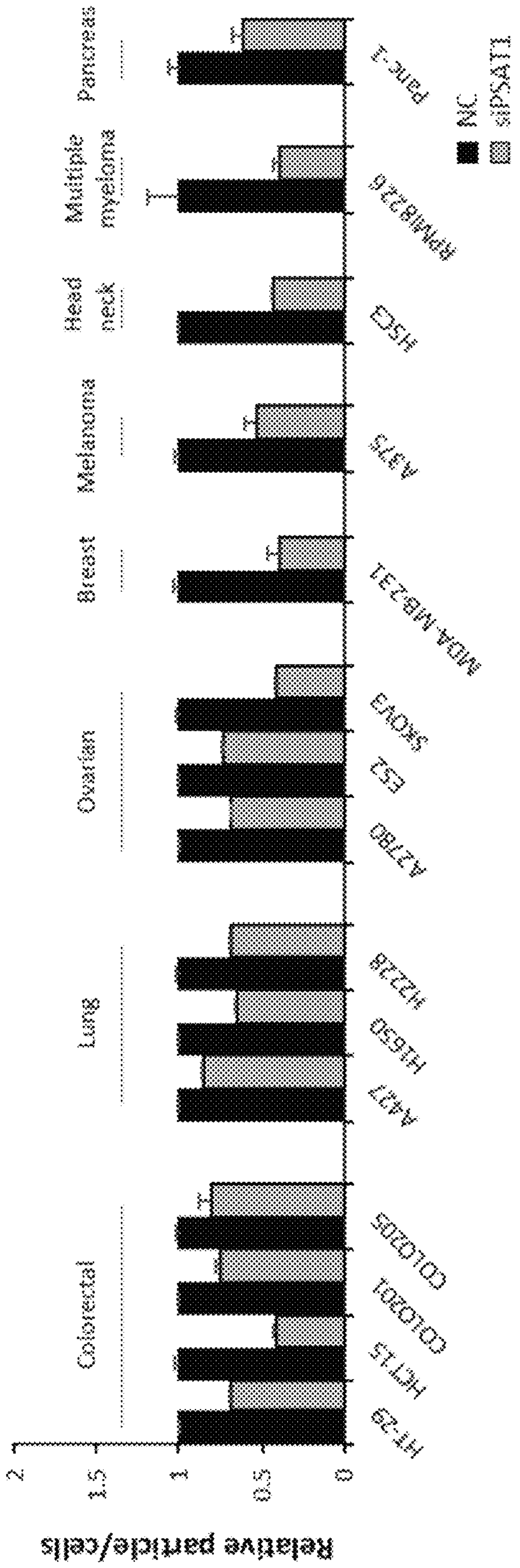
FIG. 9 shows graphs showing, regarding transformants (siPSAT1) obtained by transfecting various types of cancer cells with siPSAT1 and transformants (NC) as negative controls, the relative values of the amounts of secreted EVs measured by the NTA method.

Accordingly, in the present example, the above-described respective types of cancer cells were transfected with siRNA (siPSAT1) in the same manner as in Example A2, and the amounts of secreted EVs in the PSAT1-silenced transformants were measured by the NTA. The results obtained are shown in FIG. 9. FIG. 9 shows graphs showing the relative values of the amounts of secreted EVs measured by the NTA method.

As can be seen from FIG. 9, in the respective types of cancer cells, the amounts of the secreted EVs in the transformants (siPSAT1) transfected with siPSAT1 were significantly lower than those in transformants (NC) as negative controls. From these results, it was found that EV secretion in various types of cancer cells can be reduced by reducing the expression of PSAT1. These results confirmed that synthesis of serine is inhibited by reducing the expression of PSAT1, whereby EV secretion from various types of cancer cells can be reduced. Accordingly, it can be said that inhibiting serine synthesis by, for example, reducing the expression of PSAT1 enables treatment of these various types of cancers and prevention of metastasis of these cancers to other organs.

Example D

The present example examined reduction in tumor volume, inhibition of EV secretion, and the like in vivo using an inhibitor NCT-503 of an enzyme protein (PHGDH) in the serine synthesis pathway.

Figure 10:
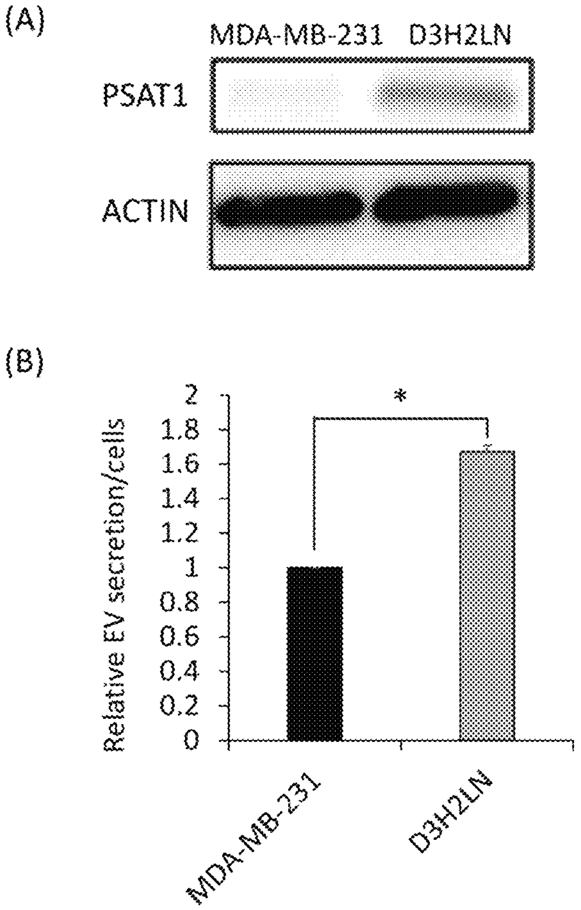
FIG. 10 shows the results regarding a breast cancer metastatic cell line MDA-MB-231_Luc_D3H2LN. (B) shows a graph showing the relative values of the amounts of secreted EVs measured by the NTA method, and (A) shows Western blot pictures indicating the expression of a PSAT1 protein.

As a breast cancer metastatic cell line, an MDA-MB-231_Luc_D3H2LN cell line (hereafter referred to as D3H2LN) was used. This cell line is a modified strain of the parent breast cancer cell line MDA-MB-231, and this cell line had been confirmed to exhibit a significantly larger amount of exosome secretion and a higher level of PSAT1 expression than the parent cell line. Specifically, the amounts of secreted EVs in the parent cell line and the D3H2LN were measured by the NTA analysis in the same manner as in Example A1, and also, expression of PSAT1 in the parent cell line and the D3H2LN were measured by Western blotting. The results obtained are shown in FIG. 10. In FIG. 10, (B) shows a graph showing the relative values of the amounts of secreted EVs measured by the NTA method, and (A) shows Western blot pictures indicating the expression of the PSAT1 protein. As can be seen from FIG. 10, the D3H2LN had been confirmed to exhibit a significantly larger amount of exosome secretion and a higher level of PSAT1 expression than the parent cell line.

Immunodeficient mice C. B-17 scid mice (female, 6-week old) were used as mice. The D3H2LN was suspended in PBS to prepare a cell suspension of $1\times10^6$ cells/100 μL. Then, on the 0th day (Day 0), 100 μL of the cell suspension was subcutaneously implanted in the mammary gland of each mouse by injection. Then, on the 7th day (Day 7), the D3H2LN cells had engrafted, and to mice of an inhibitor administration group (n=6), an NCT-503 solution (solvent: PBS) was administered by intraperitoneal injection every day at 40 mg/kg of body weight. To mice of a non-administration group (n=6, Vehicle), the same amount of PBS was administered every day instead of the NCT-503. For each of the mice in both the administration group and the non-administration group, the tumor volume in the primary lesion (mammary gland) was measured every week using an IVIS-Spectrum (Summit Pharmaceuticals International Corporation). Specifically, the tumor volume was calculated as per the mathematical expression using the longest diameter and the shortest diameter (shortest diameter×shortest diameter×longest diameter×0.5). Also, the body weight of each mouse was measured every day to determine the toxicity. On the 35th day (Day 35), the mice were sacrificed and the mammary gland as the primary lesion and the lungs as the metastatic lesion were excised from each mouse, after which the weight of the primary lesion was measured.

Figure 11:
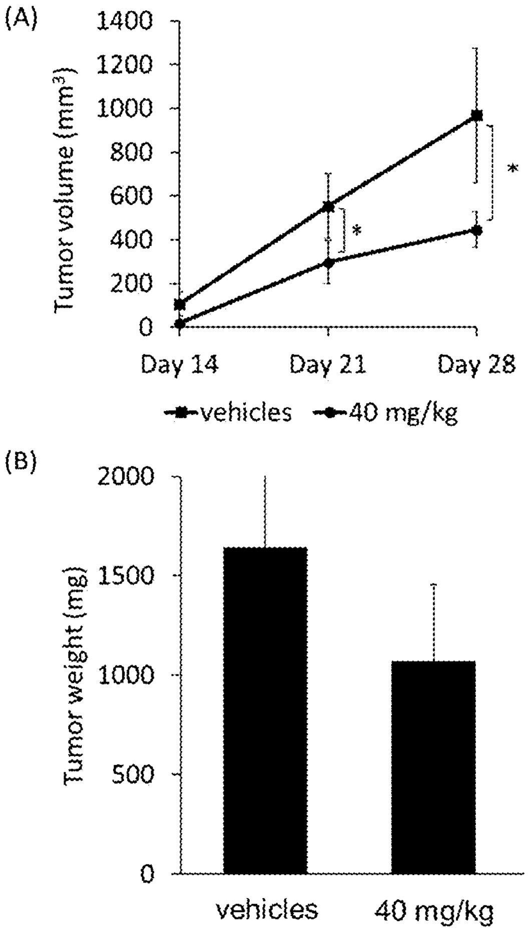
FIG. 11 shows the results regarding mice implanted with a breast cancer metastatic cell line. (A) shows a graph showing the tumor volume of the primary lesion (mammary gland) of the mice, and (B) is a graph showing the tumor weight of the primary lesion (mammary gland).

The results obtained are shown in FIG. 11. In FIG. 11, (A) shows a graph showing the tumor volume (calculated value) of the primary lesion (mammary gland) of the mice on Day 21 and Day 35, and (B) is a graph showing the tumor weight (actual measured value) of the primary lesion (mammary gland) of the mice on Day 35.

As can be seen from (A) in FIG. 11, the volume of the tumor in the primary lesion in the administration group to which the inhibitor had been administered was significantly reduced with time as compared with that in the non-administration group. Also, as can be seen from (B) in FIG. 11, the weight of the tumor in the primary lesion in the administration group to which the inhibitor had been administered was significantly reduced as compared with that in the non-administration group. In addition, the lungs as the metastatic lesion of each mouse were HE-stained. As a result, it was found that the lungs in the administration group tended to have fewer metastatic lesions than the lungs in the non-administration group.

Example E

PSAT1, which had been confirmed to reduce EV secretion in the above-described example, was used as a positive control. Regarding an enzyme protein PHGDH in the serine synthesis pathway, the present example examined the reduction of EV secretion from cancer cells by reducing the expression of the respective genes (the PHGDH gene and the PSAT1 gene). Unless otherwise stated, the examination was performed in the same manner as in Example B1 described above.

For the PHGDH gene, siPHGDH (Product No. M-9518-01-0010, Dharmacon) was used as siRNA. For the PSAT1 gene, the above-described siPSAT1 was used as in Example A.

Lung cancer cells A549 and colorectal cancer cells HCT116 were each seeded in a 96-well plate at $5\times10^3$ cells/well and in a 6-well plate at $1.5\times10^5$ cells/well (Day 0), and incubated for 24 hours. The medium used was a DMEM complete medium, which was a DMEM medium (Gibco) containing 10% heat-inactivated FBS and an antibiotic-antimycotic agent. Then, on Day 1, the respective types of cells were transfected with siRNA (siPSAT1 or siPHGDH) or the above-described ALL STAR negative control siRNA and incubated for another 24 hours. After the incubation (Day 2), the medium in the wells was replaced with an advanced DMEM medium. After another 48 hours of incubation (Day 4), the 96-well plate was used in the ExoScreen method, and the post-culture medium was collected from the 6-well plate. Secreted EVs were collected from the collected medium and then subjected to the NTA. The number of cells on the 6-well plate on Day 4 after the start of the culture were counted, and the viability was calculated assuming that the number of cells in the negative control was a relative value of 1.

Figure 12:
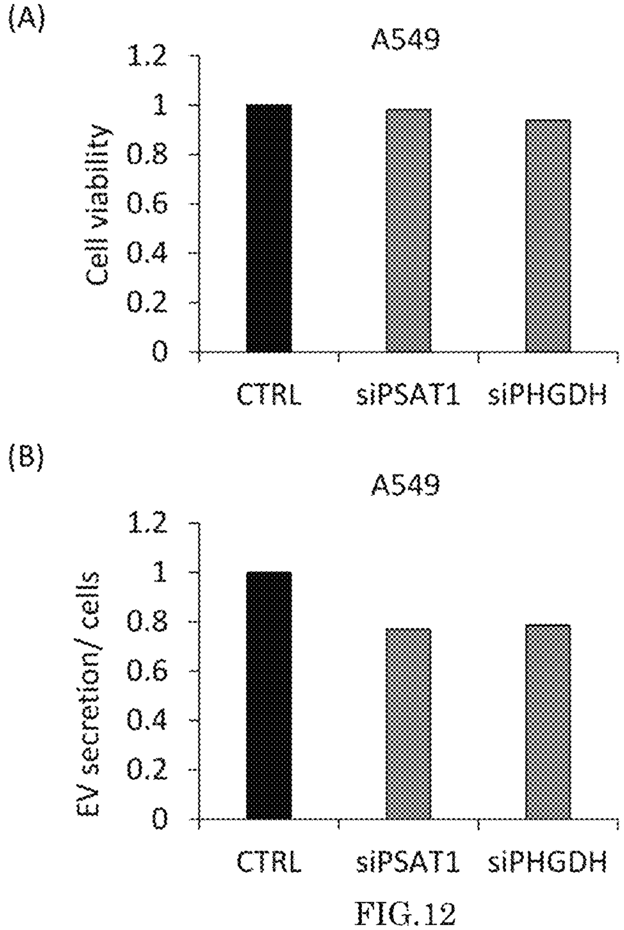
FIG. 12 shows the results regarding lung cancer cells after silencing of PSAT1 or PHGDH. (A) shows the results regarding the cell viability, (B) shows a graph showing the relative values of the amounts of secreted EVs measured by the NTA method.
Figure 13:
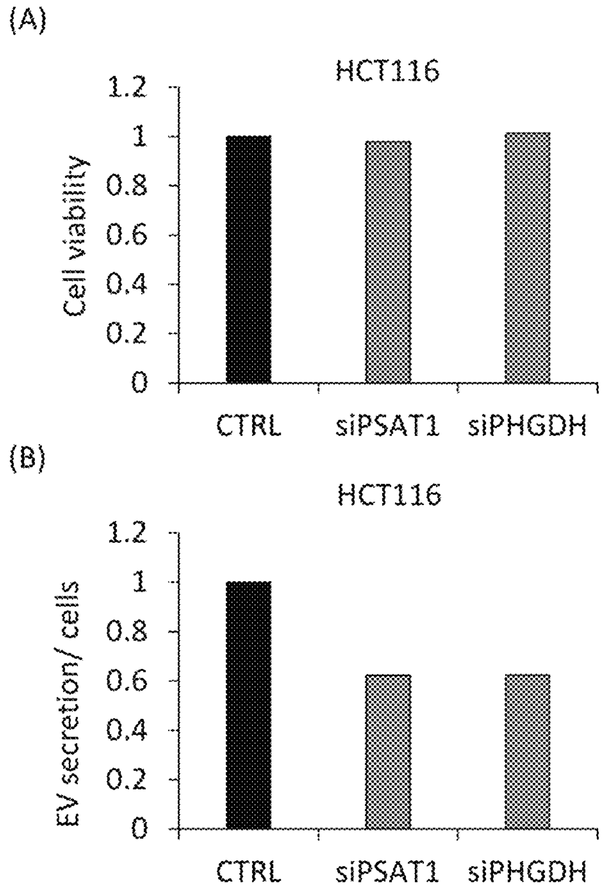
FIG. 13 shows the results regarding colorectal cancer cells after silencing of PSAT1 or PHGDH. (A) shows the results regarding the cell viability, (B) shows a graph showing the relative values of the amounts of secreted EVs measured by the NTA method.

FIG. 12 shows the results regarding the lung cancer cells A549, and FIG. 13 shows the results regarding the colorectal cancer cells HCT116. In each of FIGS. 12 and 13, (A) shows the results regarding the cell viability, and (B) shows a graph showing the relative values of the amounts of secreted EVs measured by the NTA method.

As can be seen from (A) in FIG. 12 and (A) in FIG. 13, in the both types of cancer cells, the silenced transformants showed little change in viability as compared with their unsilenced controls. Also, as can be seen from (B) and (C) in FIG. 12, the silenced transformants exhibited reduced EV secretion as compared with their controls.

Example F

Example B2 described above confirmed that EV secretion in cancer cells can be reduced by using the inhibitor NCT-503 for inhibiting PHGDH in the serine synthesis pathway. The present example presents supplemental data showing that the reduction of EV secretion was achieved not because the addition of NCT-503 caused cell death but because EV secretion specific to abnormal cells such as cancer cells is reduced by inhibiting the serine synthesis pathway.

The present example examined the effect of NCT-503 on normal cells to provide indirect data showing that NCT-503 reduced EV secretion specific to cancer cells. In Example B2 described above, NCT-503 was added to the medium in each well at 2.5 μmol/L. Thus, normal epithelial cells in each of the lung (HBEC) and the large intestine (HCoEpiC) were cultured using NCT-503-free media (containing DMSO) or NCT-503-containing media containing NCT-503 at predetermined concentrations (0.15625 to 2.5 μmol/L). Thereafter, the cell viability was determined and also the amount of secreted EVs was measured by the ExoScreen method.

Specifically, the test was performed in the following manner. The normal epithelial cells were seeded in a 96-well plate at 5000 cells/well (Day 0), and incubated for 24 hours in a medium (Day 1). The media used for the large intestinal cells were CoEpiCM 1× anti-anti media, and the media used for the lung cells were BEBM 1× anti-anti media. After the incubation, cell adhesion was confirmed, and further, the inhibitor solution (NCT-503/DMSO) was added in the same manner as in Example B2 such that the concentration of NCT-503 was 2.5 μmol/L. Further, the cells were incubated for another 48 hours (Day 3). Then, the medium in the wells was collected and the cells in the wells were counted. As a control, the same procedures as described above were performed except that DMSO was added instead of the inhibitor solution, and the cells in the wells were counted. Then, the cell viability was calculated assuming that the number of cells in the NCT-free (0 M) medium (i.e., DMSO-containing medium) of the control was a relative value of 1. Also, the amount of secreted EVs was measured by ExoScreen.

Figure 14:
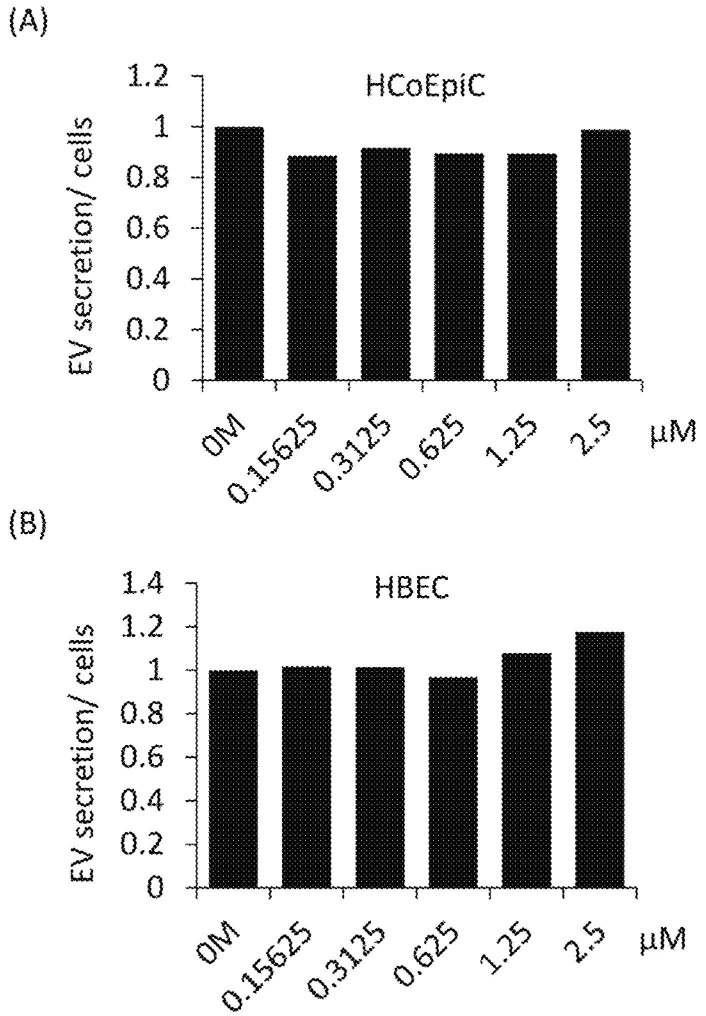
FIG. 14 shows graphs showing the amount of secreted EVs per cell. The graph shown in (A) shows the result regarding the normal epithelial cells in the large intestine, and the graph shown in (B) shows the result regarding the normal epithelial cells in the lung.

The results obtained are shown in FIG. 14. FIG. 14 shows graphs showing the amount of secreted EVs per cell. (A) shows the results regarding the normal epithelial cells in the large intestine, and (B) shows the results regarding the normal epithelial cells in the lung. As a result, regarding the normal epithelial cells in both the large intestine and the lung, there was almost no difference between the amount of secreted EVs in the NCT-503-containing medium and the amount of secreted EVs in the DMSO-containing medium without NCT (0 M). Specifically, for example, when NCT-503 was added at a concentration of 2.5 μmol/L, the relative value of the amount of secreted EVs in the NCT-503-containing medium with respect to the amount of secreted EVs in the DMSO-containing medium without NCT (0 M) was 0.98 in the case of the normal epithelium cells in the large intestine and 1.17 in the case of the normal epithelium cells in the lung, and these relative values indicate that there was almost no difference in the amount of secreted EVs between these media. In other words, the addition of NCT-503 did not affect EV secretion in the normal epithelial cells. In contrast to these results, in Example B2 described above, adding 2.5 μmol/L NCT-503 to the cancer cells could significantly reduce EV secretion as compared with the control in which only DMSO as the solvent for NCT-503 was added. These results confirm that the reduction of EV secretion by adding NCT-503 in cancer cells was achieved not because the addition of NCT-503 caused cell death but because the expression of the serine synthesis system was upregulated owing to canceration of the cells and the inhibitor NCT-503 addressed this upregulation by inhibiting PHGDH in this synthesis system, thereby reducing the EV secretion.

While the present invention has been described above with reference to illustrative embodiments and examples, the present invention is by no means limited thereto. Various changes and modifications that may become apparent to those skilled in the art may be made in the configuration and specifics of the present invention without departing from the scope of the present invention.

This application claims priority from Japanese Patent Application No. 2020-069392 filed on Apr. 7, 2020 and Japanese Patent Application No. 2021-022825 filed on Feb. 16, 2021. The entire disclosures of these Japanese patent applications are incorporated herein by reference.

INDUSTRIAL APPLICABILITY

According to the present invention, extracellular vesicle secretion from cells can be reduced by inhibiting the serine synthesis pathway. Thus, reducing the secretion according to the present invention enables the analysis of the influence of the extracellular vesicle secretion or the influence of reducing the extracellular vesicle secretion on a living organism. Therefore, it can be said that the present invention is very useful in the medical field, for example.

SEQUENCE LISTING

THS20004WO_ST25.txt

The invention claimed is:

1. A method for reducing extracellular vesicle secretion from a cell, comprising:

exposing the cell to an extracellular vesicle secretion reducing agent comprising an inhibitor of a serine synthesis pathway for reducing extracellular vesicle secretion from the cell.

2. The method according to claim 1, wherein the cell is a cancer cell.

3. The method according to claim 2, wherein the cancer cell is at least one selected from the group consisting of colorectal cancer cells, lung cancer cells, melanoma cells, breast cancer cells, pancreas cancer cells, and multiple myeloma cells.

4. The method according to claim 1, wherein the cell is a virus-infected cell.

* * * * *

```
                         SEQUENCE LISTING


<160> NUMBER OF SEQ ID NOS: 2

<210> SEQ ID NO 1
<211> LENGTH: 21
<212> TYPE: RNA
<213> ORGANISM: Artificial Sequence
<220> FEATURE:
<223> OTHER INFORMATION: miRNA for PSAT1
<220> FEATURE:
<221> NAME/KEY: miR-891b
<222> LOCATION: (1)..(21)

<400> SEQUENCE: 1

gcaacuuacc ugagucauug a                                              21


<210> SEQ ID NO 2
<211> LENGTH: 22
<212> TYPE: RNA
<213> ORGANISM: Homo sapiens
<220> FEATURE:
<221> NAME/KEY: 3'UTR
<222> LOCATION: (1)..(22)

<400> SEQUENCE: 2

uggacuuaau aaugcaaguu gc                                             22
```